(12) United States Patent
Heien et al.

(10) Patent No.: US 10,874,334 B1
(45) Date of Patent: Dec. 29, 2020

(54) METHODS AND SYSTEMS FOR QUANTIFICATION OF BLOOD-BRAIN BARRIER PERMEATION OF GLYCOSYLATED PEPTIDES

(71) Applicant: ARIZONA BOARD OF REGENTS ON BEHALF OF THE UNIVERSITY OF ARIZONA, Tucson, AZ (US)

(72) Inventors: Michael L. Heien, Tucson, AZ (US); Nicholas D. Laude, Tucson, AZ (US); Catherine L. Kramer, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 473 days.

(21) Appl. No.: 15/674,320

(22) Filed: Aug. 10, 2017

Related U.S. Application Data

(60) Provisional application No. 62/373,231, filed on Aug. 10, 2016.

(51) Int. Cl.
| | |
|---|---|
| *A61B 5/145* | (2006.01) |
| *A61B 5/00* | (2006.01) |
| *A61B 10/00* | (2006.01) |
| *A61K 38/08* | (2019.01) |
| *A61M 1/16* | (2006.01) |
| *G01N 30/72* | (2006.01) |
| *B01D 61/24* | (2006.01) |

(Continued)

(52) U.S. Cl.
CPC ........ *A61B 5/14528* (2013.01); *A61B 5/0002* (2013.01); *A61B 10/0045* (2013.01); *A61K 38/08* (2013.01); *A61M 1/1603* (2014.02); *B01D 61/246* (2013.01); *B01D 61/30* (2013.01); *G01N 30/02* (2013.01); *G01N 30/7206* (2013.01); *G01N 2030/027* (2013.01); *G01N 2030/8822* (2013.01)

(58) Field of Classification Search
CPC ... C07C 309/15; C07C 309/24; C07C 309/18; C07C 309/19; C07C 309/14; A61K 31/145; A61K 47/54; A61K 47/542; A61K 47/545; A61K 47/549; A61K 47/554; A61K 47/64; A61K 31/18; A61K 47/48023; A61K 47/48092; A61K 38/08; A61B 5/14528; A61B 5/0002; A61B 10/0045; A61M 1/1603; B01D 61/30; G01N 30/02; G01N 30/7206; G01N 2030/027; G01N 2030/8822
See application file for complete search history.

(56) References Cited

U.S. PATENT DOCUMENTS

| | | | |
|---|---|---|---|
| 5,865,766 A * | 2/1999 | Bonsall | A01K 1/031 600/578 |
| 2015/0030576 A1* | 1/2015 | Bancel | A61K 35/17 424/93.21 |
| 2016/0304577 A1* | 10/2016 | Goletz | A61K 47/6425 |

* cited by examiner

*Primary Examiner* — Brandy S Lee
(74) *Attorney, Agent, or Firm* — Nguyen Tarbet LLC

(57) ABSTRACT

Methods and systems for quantifying blood brain barrier (BBB) permeation of glycosylated peptides. The methods and systems feature microdialysis probes and mechanisms for infusing preservative agents into the outflow tubes of the microdialysis probes. The preservative agents help reduce unwanted degradation of the glycosylated peptides or other compounds, which can lead to a more accurate and complete analysis of the outflow tube perfusate.

7 Claims, 4 Drawing Sheets

(51) Int. Cl.
*B01D 61/30* (2006.01)
*G01N 30/02* (2006.01)
*G01N 30/88* (2006.01)

METHODS AND SYSTEMS FOR QUANTIFICATION OF BLOOD-BRAIN BARRIER PERMEATION OF GLYCOSYLATED PEPTIDES

CROSS REFERENCE

This application claims priority to U.S. Provisional Patent Application No. 62/373,231 filed Aug. 10, 2016, the specification(s) of which is/are incorporated herein in their entirety by reference.

FIELD OF THE INVENTION

The present invention relates to methods and systems for quantifying permeation of glycosylated peptides through the blood-brain barrier, more particularly to methods and systems featuring microdialysis coupled with mass spectrometry for quantification of blood-brain barrier permeation of glycosylated peptides.

BACKGROUND OF THE INVENTION

Endogenous opioid peptide-based drugs show promise in anti-nociception therapeutics. However, they are vulnerable to enzymatic degradation and typically have poor blood-brain barrier (BBB) penetration. Studies have shown improved permeation of the BBB with glycosylated peptides.

The extent to which a substance in the circulation can access to the brain typically can be via brain microdialysis. In this process, a microdialysis probe (with a dialysis membrane) is implanted in the brain, and perfusate having passed through the membrane is collected in a collection tube (outflow tube) and subsequently analyzed. In this method, however, degradation of peptides or other compounds in the perfusate can occur inside the outflow tube, even before preservative agents can be introduced. This degradation can cause inaccurate and/or incomplete results.

The present invention features methods and systems for quantifying BBB permeation of glycosylated peptides wherein preservative agents can be infused directly into the outflow tube to help reduce unwanted degradation of the glycosylated peptides.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

Referring to FIG. 3B, the present invention features microdialysis probe systems. In some embodiments, the probe system comprises a dialysis membrane; an inlet tube fluidly connected to the dialysis membrane such that a dialysis solution flows to the dialysis membrane; an outflow tube fluidly connected to the dialysis membrane such that outflow fluid flows away from the dialysis membrane; and an infuser tube fluidly connected to the outflow tube, wherein the infuser tube directs a preservation fluid into the outflow tube where the preservation fluid combines with the outflow fluid. The preservation fluid comprises a preservative agent that inhibits or reduces degradation of glycosylated peptides present in the outflow fluid in the outflow tube.

In some embodiments, the preservative agent comprises acetic acid, formic acid, or a combination thereof. In some embodiments, the preservation fluid comprises from 5% to 10% acetic acid. In some embodiments, the preservation fluid further comprises [Dala$^2$,Dleu$^5$] enkephalin (DADLE). In some embodiments, the dialysis solution comprises isotonic artificial cerebrospinal fluid (aCSF).

In some embodiments, the probe system further comprises a first syringe pump fluidly connected to the inlet tube, wherein the first syringe pump pumps the dialysis fluid through the inlet tube to the dialysis membrane. In some embodiments, the probe system further comprises a second syringe pump fluidly connected to the infuser tube, wherein the second syringe pump pumps the preservation fluid through the infuser tube to the outflow tube. In some embodiments, the probe system further comprises a micro-tee adaptor placed after the microdialysis probe, wherein the micro-tee adaptor combines the preservation fluid with the outflow fluid. In some embodiments, the probe system further comprises a fraction collector disposed downstream from wherein the preservation fluid and outflow fluid combine. In some embodiments, the probe system further comprises a multi-fluid-line swivel for integrating the inlet tube, the outflow tube, and the infuser tube.

In some embodiments, the probe system further comprises a detection component downstream of the outflow tube or downstream of the fraction collector, wherein the detection component detects endogenous opioid peptides (EOPs). The probe system of the present invention may allow for quantification of the EOPs. The probe system of the present invention may allow for quantification of EOPs at concentrations of 10 pM or less. In some embodiments, the probe system has a detection limit of 1.5 amol. In some embodiments, the detection component performs nano LC-MS$''$ identification and quantification.

The present invention also features methods of preserving endogenous opioid peptides (EOPs). In some embodiments, the method comprises implanting into a brain of a subject a microdialysis probe system of the present invention, wherein the dialysis membrane is implanted into an implantation site of the brain; and pumping the dialysis solution through the inlet tube to the dialysis membrane and pumping preservative fluid through the infuser tube to the outflow tube. When the preservative fluid combines with outflow fluid in the outflow tube, the preservative fluid inhibits or reduces degradation of the EOP thereby preserving the EOP.

The present invention also features methods of detecting or quantifying endogenous opioid peptides (EOPs). In some embodiments, the method comprises implanting into a brain of a subject a microdialysis probe system of the present invention, wherein the dialysis membrane is implanted into an implantation site of the brain; pumping the dialysis solution through the inlet tube to the dialysis membrane and pumping preservative fluid through the infuser tube to the outflow tube, wherein when the preservative fluid combines with outflow fluid in the outflow tube, the preservative fluid inhibits or reduces degradation of the EOP; and performing nano liquid chromatography-mass spectrometry (LC-MS$''$) on the outflow fluid, wherein nano LC-MS$''$ can detect the presence of the EOP or quantify the EOP.

In some embodiments, the implantation site is an anterior cingulate cortex or striatum. In some embodiments, the EOP comprises methionine sulphoxide enkephalin (MSE), methionine enkephalin (ME), leucine enkephalin (LE), or endomorphin II (EM II), or a combination thereof.

BRIEF DESCRIPTION OF THE DRAWINGS

The features and advantages of the present invention will become apparent from a consideration of the following detailed description presented in connection with the accompanying drawings in which:

FIG. 4A shows species that were monitored and detected in the animals: 1 methionine sulphoxide enkephalin (MSE), 2 methionine enkephalin (ME), 3 leucine enkephalin (LE), and 4 endomorphin II (EM II). Key structural differences in the species are highlighted. The internal standard, 5 [Dala$^2$, Dleu$^5$] enkephalin (DADLE), is continuously present in the online preservation fluid and allows the variation in microdialysis flow rate, recovery during sample preparation, and ionization efficiency to be accounted for.

DETAILED DESCRIPTION OF THE INVENTION

As previously discussed, glycosylated peptides have improved permeation of the blood brain barrier (BBB) as compared to their un-glycosylated counterparts. The present invention features methods and systems for quantifying BBB permeation of glycosylated peptides wherein preservative agents can be infused directly into the outflow tube to help reduce unwanted degradation of the glycosylated peptides. This system may also be coupled with mass spectrometry for detection purposes.

In some embodiments, the preservative comprises acetic acid, formic acid, a specific enzyme inhibitor, or a combination thereof. The present invention is not limited to these preservatives.

Figure 1A:
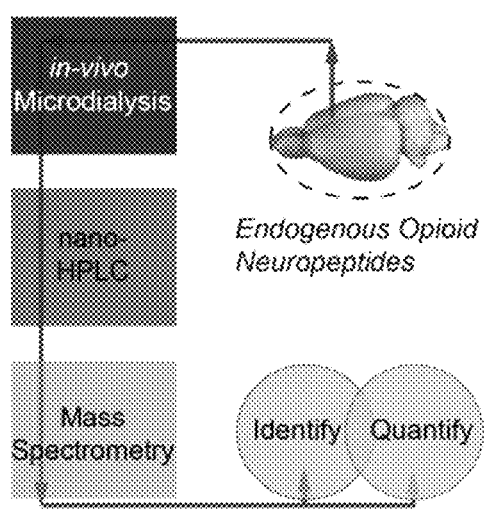
FIG. 1A shows a schematic of a workflow of the present invention. Endogenous Opioid Peptides (EOPs) exist at low but unknown concentrations in vivo. The workflow of the present invention features a quantitative analysis that gives highly selective identification (spectral fingerprint) and extremely sensitive quantification (<10 pM concentrations). EOP measurements are achieved using in vivo microdialysis with nano LC-MS$^n$ identification & quantification
Figure 1B:
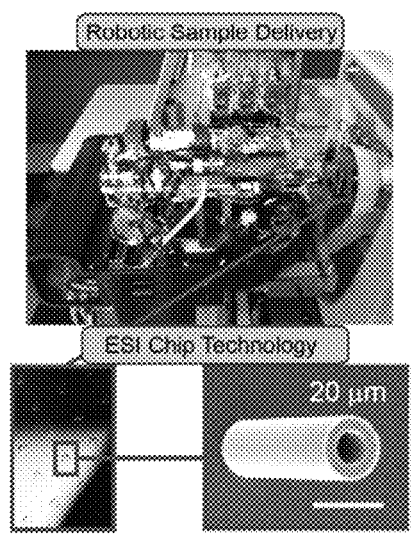
FIG. 1B shows a schematic view of the present invention, e.g., ESI Chip technology.
Figure 1C:
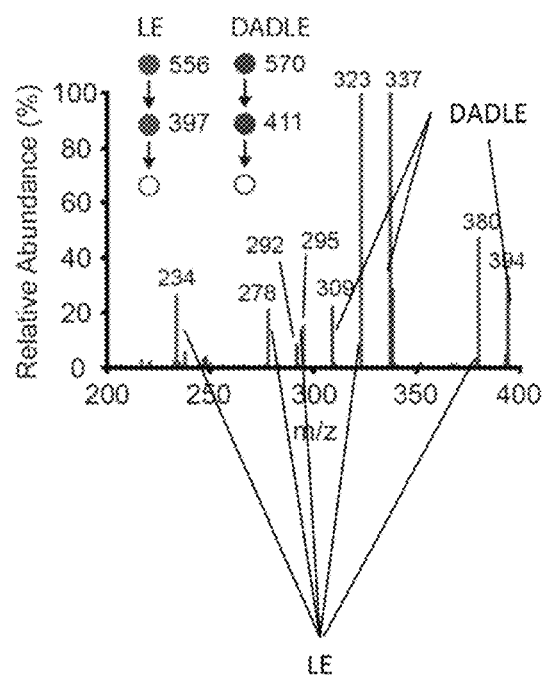
FIG. 1C shows the MS$^3$ spectra of leucine enkephalin (LE) and the internal standard DADLE with ion transitions labeled.

Endogenous Opioid Peptides (EOPs) exist at low but unknown concentrations in vivo, thus a workflow for quantitative analysis must give highly selective identification (spectral fingerprint) and extremely sensitive quantification (<10 pM concentrations). EOP measurements are achieved using in vivo microdialysis with nano LC-MS$^n$ identification & quantification (see FIG. 1A). As brain regions with relatively low concentration of EOPs are explored using advanced robotic sample delivery and chip-based electrospray ionization (ESI Chip) technology increases the sensitivity of mass spectrometry and increases reproducibility, thus reducing error (see FIG. 1B). Micrographs of ESI Chip nozzles are adapted with permission from Advion, Inc.

Figure 1D:
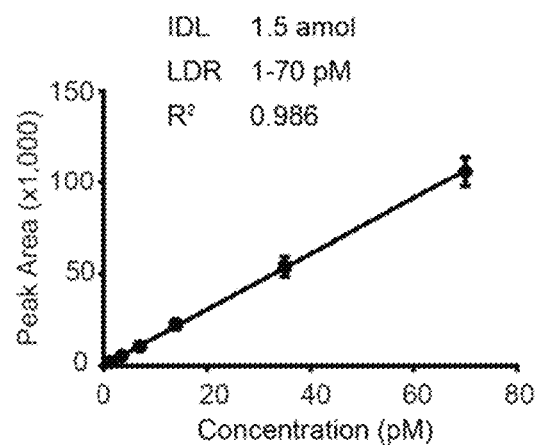
FIG. 1D shows a linear dynamic range (LDR) for LE extending from 1-70 pM. The instrument detection limit (IDL) is incredibly low (1.5 amol) due to the pre-concentration and high ionization efficiency achieved with the ESI Chip.

Highly selective tandem mass spectrometry ($MS^3$) allows for a characteristic spectral fingerprint of each molecule to be extracted from complicated biological matrix. The $MS^3$ spectra of leucine enkephalin (LE) and the internal standard DADLE are shown with ion transitions labeled (see FIG. 10). The technique is highly quantitative with a linear dynamic range (LDR) for LE extending from 1-70 pM. The instrument detection limit (IDL) is incredibly low (1.5 amol) due to the pre-concentration and high ionization efficiency achieved with the ESI Chip (see FIG. 1D).

Figure 2A:
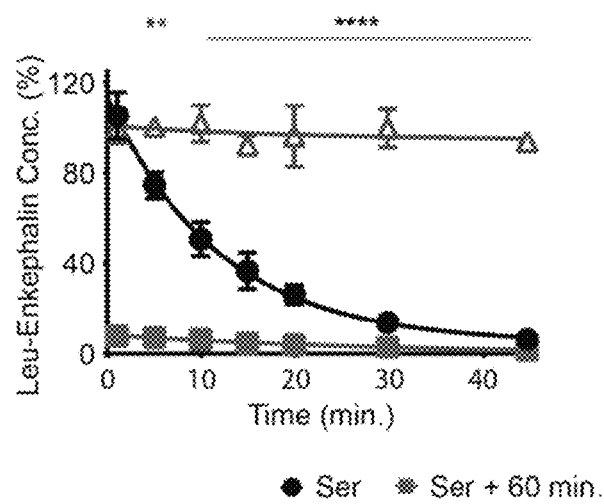
FIG. 2A shows a degradation study of Leu-enkephalin spiked into rodent serum (performed by FIA-MS$^n$). Ser refers to when Enkephalins were added to rat serum and degradation was allowed to proceed and the remaining enkephalin levels were measured at specific time points. Ser+60 min refers to when peptides were incubated in serum for 60 minutes prior to the study (note: degradation was already complete before analysis could take place). Ser+HAc+60 min refers to when 5% acetic acid (HAc) was added to the serum, preserving enkephalins by inhibiting degradation during a 60 minute period before beginning measurements (Ser+HAc+60 min.). All error bars are SEM. Statistical significance is indicated by asterisks when $p<0.05$.
Figure 2B:
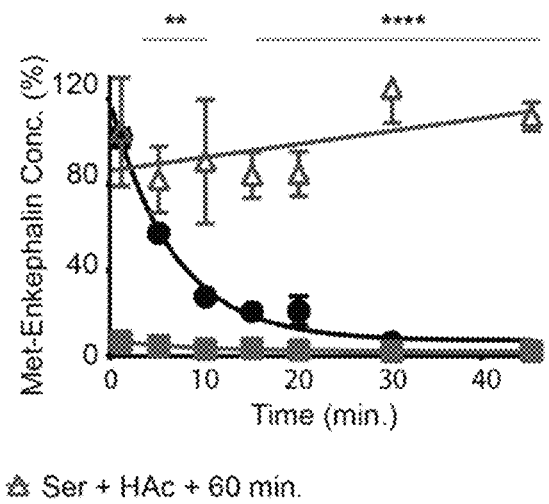
FIG. 2B shows a degradation study of Met-enkephalin spiked into rodent serum (performed by FIA-MS$^n$). Ser refers to when Enkephalins were added to rat serum and degradation was allowed to proceed and the remaining enkephalin levels were measured at specific time points. Ser+60 min refers to when peptides were incubated in serum for 60 minutes prior to the study (note: degradation was already complete before analysis could take place). Ser+HAc+60 min refers to when 5% acetic acid (HAc) was added to the serum, preserving enkephalins by inhibiting degradation during a 60 minute period before beginning measurements (Ser+HAc+60 min.). All error bars are SEM. Statistical significance is indicated by asterisks when $p<0.05$.
Figure 2C:
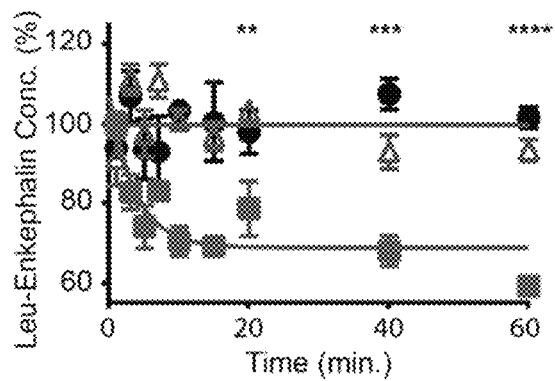
FIG. 2C shows a degradation study of Leu-enkephalin spiked into cerebral spinal fluid (CSF) from rats. +CSF refers to when the peptides were added to CSF; aCSF refers to an isotonic artificial CSF (aCSF) solution; and +CSF+HAc refers to when 5% HAc was added, preventing the degradation of the peptide. All error bars are SEM. Statistical significance is indicated by asterisks when $p<0.05$.
Figure 2D:
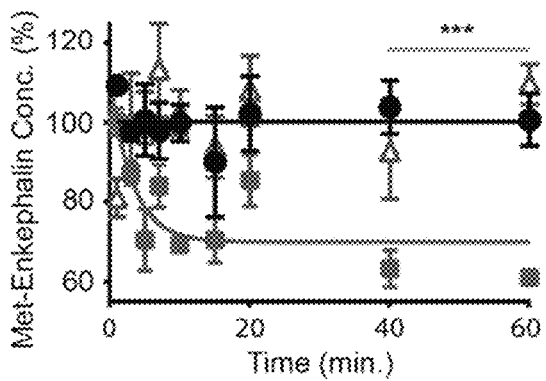
FIG. 2D shows a degradation study of Met-enkephalin spiked into cerebral spinal fluid (CSF) from rats. +CSF refers to when the peptides were added to CSF; aCSF refers to an isotonic aCSF solution; and +CSF+HAc refers to when 5% HAc was added, preventing the degradation of the peptide. All error bars are SEM. Statistical significance is indicated by asterisks when $p<0.05$.

Degradation studies of enkephalins in biological fluids were performed by HA-$MS^n$. The stability of Leu and Met-Enkephalin spiked into rodent serum were studied under different treatment conditions (see FIG. 2A and FIG. 2B, respectively). Enkephalins were added to rat serum and degradation was allowed to proceed and the remaining enkephalin levels were measured at specific time points (Ser). When peptides were incubated in serum for 60 minutes prior to the study, degradation was already complete before analysis could take place (Ser+60 min.). Addition of 5% acetic acid (HAc) to the serum preserved enkephalins by inhibiting degradation during a 60-minute period before beginning measurements (Ser+HAc+60 min.). Carrying out these degradation experiments using cerebral spinal fluid (CSF) from rats showed that Leu and Met-Enkephalin degradation occurs in CSF over 20 minutes (see FIG. 2C and FIG. 2D, +CSF). These data were fit with a single exponential decay to highlight the degradation. Addition of 5% HAc prevents the degradation (+CSF+HAc) showing that enkephalin stability is the same as in an isotonic aCSF solution (aCSF) and these data are fit around the line at 100% concentration.

Figure 3A:
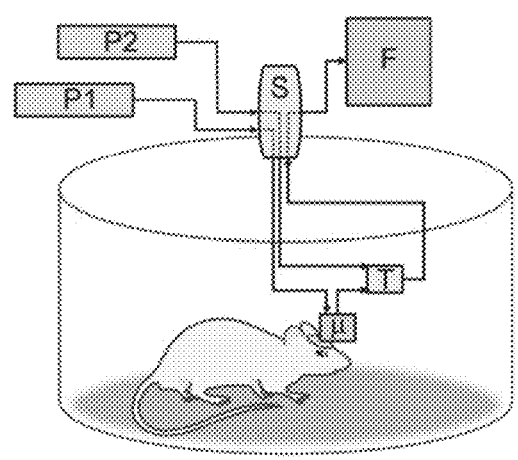
FIG. 3A shows a schematic of the apparatus that utilizes two syringe pumps (P1, P2). Isotonic aCSF is delivered through P1 and preservation fluid is delivered through P2. Because of the additional fluid lines, a multi-fluid-line swivel (5) was used. A micro-tee adaptor (T) was placed after the microdialysis probe (p) to combine the preservation fluid with the dialysate to achieve preservation before the sample travels through the fraction collector (F).
Figure 3B:
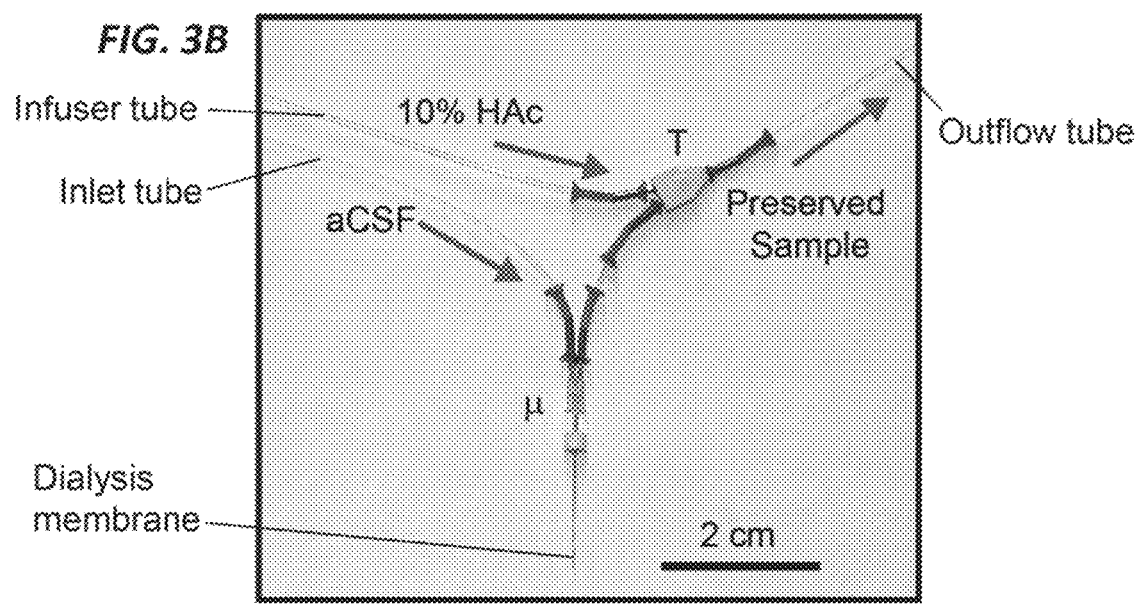
FIG. 3B shows a photograph of the online preservation micro-T and dialysis probe of FIG. 3A.
Figure 3C:
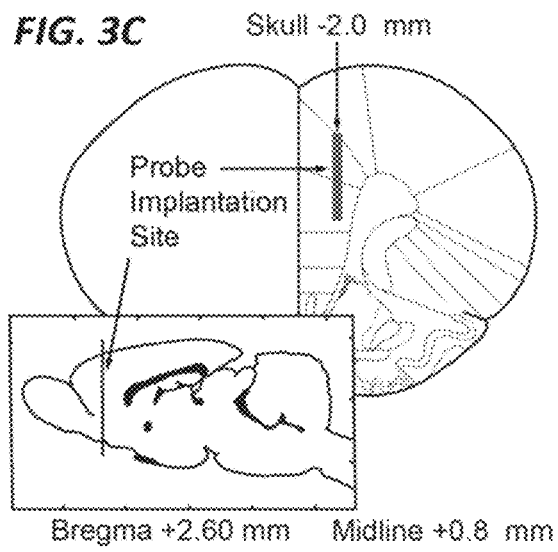
FIG. 3C shows the implantation site of the microdialysis probe, shown with stereotaxic coordinate on the sagittal (left) and coronal (center background) slice diagrams.
Figure 3D:
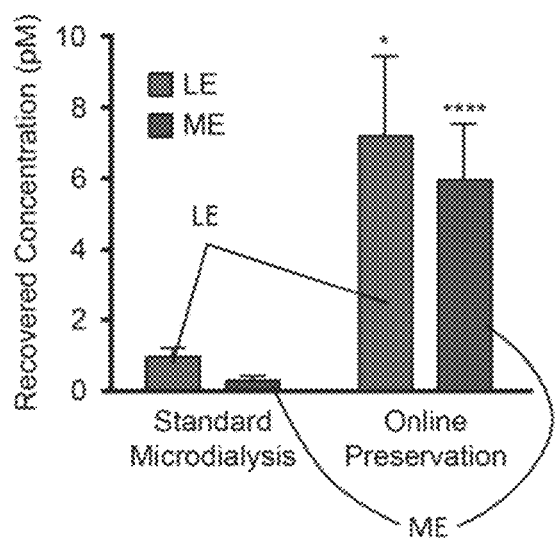
FIG. 3D shows the concentration of recovered peptide (Leu-Enkephalin. LE; Met-Enkephalin, ME). Note: n=3 animals, error bars SEM, asterisks denote $p<0.05$.

On-line preservation apparatus scheme allows for improved microdialysis recoveries from the anterior cingulate cortex. The apparatus (shown in FIG. 3A) utilizes two syringe pumps (P1, P2): isotonic aCSF delivered through P1 and preservation fluid through P2. Because of the additional fluid lines, a multi-fluid-line swivel (S) was used. A micro-tee adaptor (T) is placed after the microdialysis probe (p) to combine the preservation fluid with the dialysate to achieve preservation before the sample travels through the fraction collector (F). A photograph of the online preservation micro-T and dialysis probe is shown in FIG. 3B. The implantation site of the microdialysis probe (FIG. 3O) is shown with stereotaxic coordinate on the sagittal (left) and coronal (center background) slice diagrams. The result of online preservation was a large increase in measured concentration (see FIG. 3D), presumably due to the inhibition of enzyme activity as is evidenced in FIG. 2A-2D.

Figure 4A:
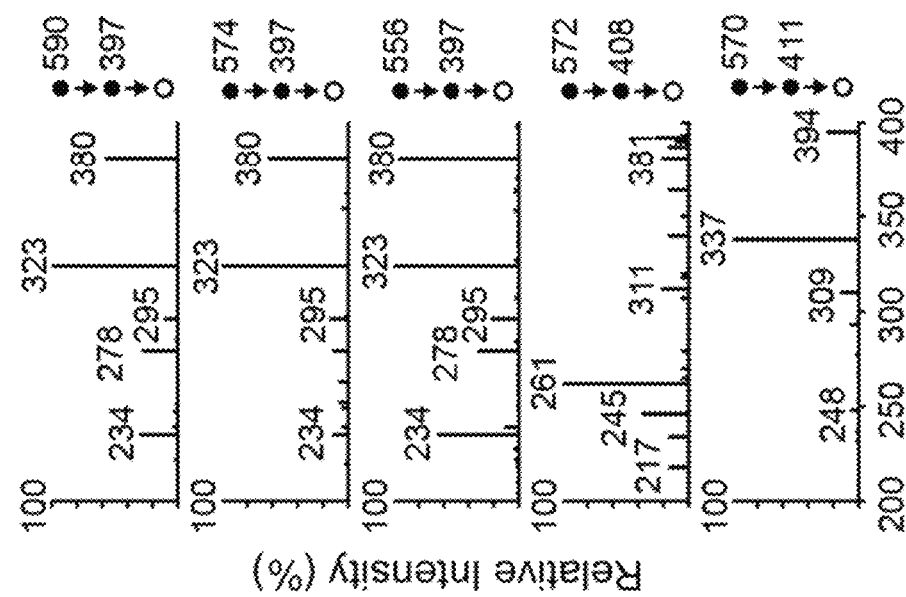
Figure 4B:
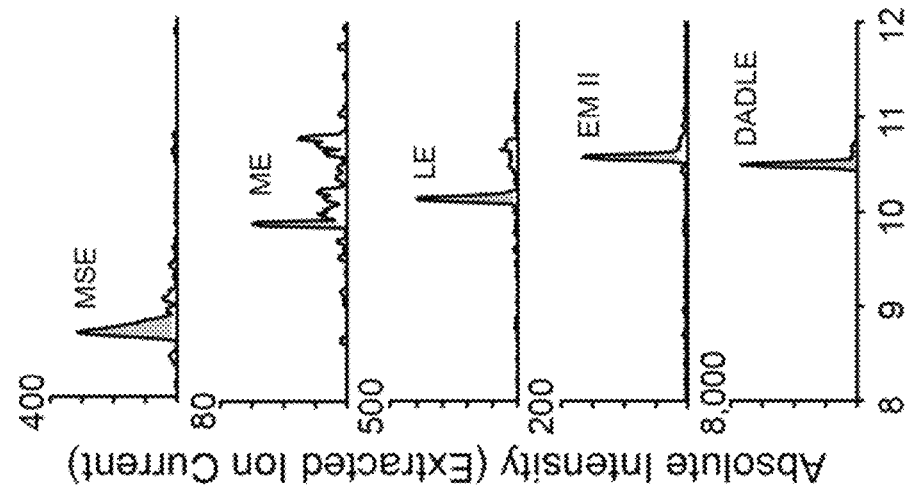
FIG. 4B shows a baseline Extracted Ion Chromatogram for each of the five peptides of FIG. 4A involved in quantification. The grey shaded areas under the peaks represent the integrated region for quantification.
Figure 4C:
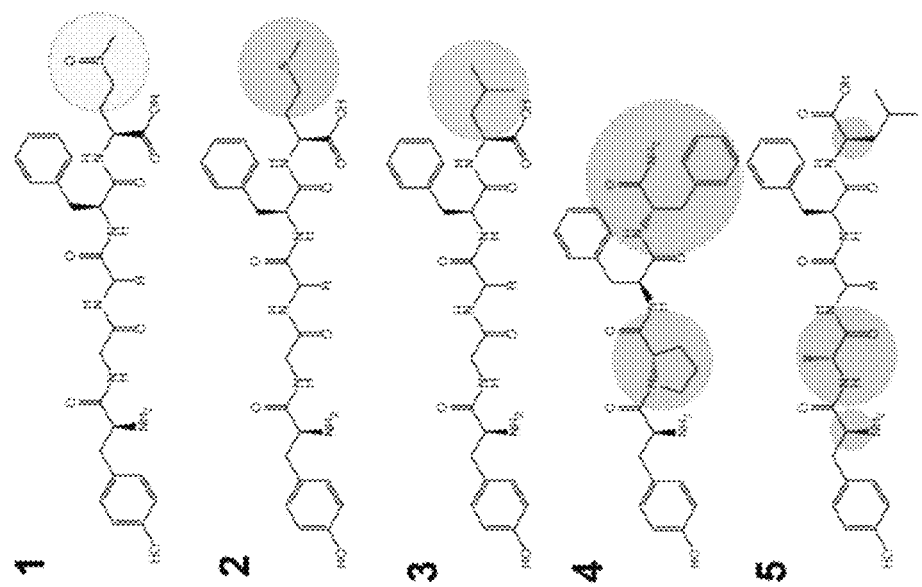
FIG. 4C shows mass spectra from in vivo samples to confirm the identity of the analyte being quantified. The corresponding ion transitions are shown to the right of the MS$^3$ spectrum for each peptide and the m/z of the specific fragment ions used to quantify each neuropeptide are labeled in the mass spectrum.

Four endogenous species were monitored and detected from the animals (rat anterior cingulate cortex): 1 methionine sulphoxide enkephalin (MSE), 2 methionine enkephalin (ME), 3 leucine enkephalin (LE), and 4 endomorphin H (EM H). The structures of these peptides are shown in FIG. 4A with key structural differences highlighted. The internal standard, 5 [$Dala^2$,$Dleu^5$] enkephalin (DADLE), is continuously present in the online preservation fluid and allows the variation in microdialysis flow rate, recovery during sample preparation, and ionization efficiency to be accounted for. A baseline Extracted Ion Chromatogram is shown for each of the five peptides involved in quantification (see FIG. 4B). The grey shaded areas under the peaks represent the integrated region for quantification. Mass spectra from in vivo samples corresponding to the shaded area confirm the identity of the analyte being quantified (see FIG. 4C). The corresponding ion transitions are shown to the right of the $MS^3$ spectrum for each peptide and the m/z of the specific fragment ions used to quantify each neuropeptide are labeled in the mass spectrum.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A microdialysis probe system comprising:
   a. a dialysis membrane;
   b. an inlet tube fluidly connected to the dialysis membrane such that a dialysis solution flows to the dialysis membrane;
   c. an outflow tube fluidly connected to the dialysis membrane such that outflow fluid flows away from the dialysis membrane;
   d. an infuser tube fluidly connected to the outflow tube, the infuser tube directs a preservation fluid into the outflow tube, wherein the preservation fluid combines with the outflow fluid, the preservation fluid comprises a preservative agent that inhibits or reduces degradation of glycosylated peptides present in the outflow fluid in the outflow tube; and
   e. a detection component downstream of the outflow tube, the detection component detecting endogenous opioid peptides (EOPs).

2. The probe system of claim 1, wherein the probe system allows for quantification of the EOPs.

3. The probe system of claim 2, wherein the probe system allows for quantification of the EOPs at concentrations of 10 pM or less.

4. The probe system of claim 2, wherein the probe system has a detection limit of 1.5 amol.

5. The probe system of claim 1 further comprising:
   a. a first syringe pump fluidly connected to the inlet tube, the first syringe pump pumps the dialysis fluid through the inlet tube to the dialysis membrane;
   b. a second syringe pump fluidly connected to the infuser tube, the second syringe pump pumps the preservation fluid through the infuser tube to the outflow tube; and c. a micro-tee adaptor placed after the microdialysis probe, the micro-tee adaptor combines the preservation fluid with the outflow fluid.

6. The probe system of claim 5 further comprising a fraction collector disposed downstream from wherein the preservation fluid and outflow fluid combine.

7. The probe system of claim 5 further comprising a multi-fluid-line swivel for integrating the inlet tube, the outflow tube, and the infuser tube.

* * * * *